United States Patent
Qi et al.

(10) Patent No.: US 10,502,748 B2
(45) Date of Patent: Dec. 10, 2019

(54) METHOD OF DIFFERENTIATING STABLE ANGINA PECTORIS FROM ACUTE CORONARY SYNDROME AND DIAGNOSTIC KIT THEREOF

(71) Applicant: Lianwen Qi, Nanjing (CN)

(72) Inventors: Lianwen Qi, Nanjing (CN); Yong Fan, Nanjing (CN); Ping Li, Nanjing (CN); Wei Zhu, Nanjing (CN); Yan Chen, Nanjing (CN)

(73) Assignee: Lianwen Qi, Nanjing (CN)

( * ) Notice: Subject to any disclaimer, the term of this patent is extended or adjusted under 35 U.S.C. 154(b) by 161 days.

(21) Appl. No.: 15/599,419

(22) Filed: May 18, 2017

(65) Prior Publication Data

US 2018/0088132 A1 Mar. 29, 2018

Related U.S. Application Data

(63) Continuation-in-part of application No. 15/273,728, filed on Sep. 23, 2016, now abandoned.

(51) Int. Cl.

| | |
|---|---|
| *G01N 33/68* | (2006.01) |
| *G01N 33/92* | (2006.01) |
| *G01N 33/88* | (2006.01) |
| *G01N 33/49* | (2006.01) |
| *G01N 30/72* | (2006.01) |
| *G01N 30/88* | (2006.01) |
| *G16H 50/20* | (2018.01) |

(52) U.S. Cl.
CPC ..... *G01N 33/6893* (2013.01); *G01N 30/7206* (2013.01); *G01N 33/492* (2013.01); *G01N 33/6815* (2013.01); *G01N 33/88* (2013.01); *G01N 33/92* (2013.01); G01N 30/7233 (2013.01); G01N 2030/8822 (2013.01); G01N 2560/00 (2013.01); G01N 2570/00 (2013.01); G01N 2800/324 (2013.01); G16H 50/20 (2018.01)

(58) Field of Classification Search
CPC ............. G01N 33/492; G01N 2570/00; G01N 2800/324
See application file for complete search history.

(56) References Cited

PUBLICATIONS

Barderas, Maria G. et al. "Metabolomic profiling for identification of novel potential biomarkers in cardivascular diseases." Journal of Biomedicine and Biotechnology (2011) 790132. (Year: 2011).*
Conti, C. R. et al. "Acute myocardial ischemia: role of atherosclerosis, thrombosis, platelet activation, coronary vasospasm, and altered arachidonic acid metabolism." Circulation (1987) 75 v84-v95. (Year: 1987).*
Sargent, Mike. Guide to Achieving reliable quantitative LS-MS measurements, RSC Analytical Methods Committee, 2013. (Year: 2013).*
Shimadzu. "Analysis of metabolites in human serum using GC-MS" Application Data Sheet 89 (2013). (Year: 2013).*
Xiao, Jun Feng et al. "Metabolite identification and quantitation in LC-MS/MS based metabolomics." Trends in Analytical Chemistry (2012) 1-14. (Year: 2012).*
Rongwen Shu et al, Research on the Differences in Clinical Diagnosis of Coronary Heart Disease by Using Coronary Angiography Gold Standards and Conventional Diagnosis.

* cited by examiner

*Primary Examiner* — Christopher Adam Hixson
(74) *Attorney, Agent, or Firm* — Gokalp Bayramoglu

(57) ABSTRACT

This application discloses a method of differentiating stable angina pectoris from acute coronary syndrome, including: obtaining a blood plasma sample from a patient; measuring a relative concentration of at least one metabolic biomarker in the blood plasma sample, wherein the at least one metabolic biomarker is selected from the group consisting of malic acid, taurine, arachidonic acid, citramalic acid, methionine, and pentadecanoic acid; calculating a value according to the relative concentration of at least one metabolic biomarker; comparing the value with a predefined critical value, if the value is more than the predefined critical value, the patient has the acute coronary syndrome, otherwise, the patient has the stable angina pectoris. The method and a diagnostic kit thereof is capable of differential diagnosis of SA and ACS and it can improve the diagnostic convenience and promote the diagnostic standardization.

6 Claims, 2 Drawing Sheets

METHOD OF DIFFERENTIATING STABLE ANGINA PECTORIS FROM ACUTE CORONARY SYNDROME AND DIAGNOSTIC KIT THEREOF

TECHNICAL FIELD

The present invention relates to biochemistry field, in particular, relates to a method of differentiating stable angina pectoris from acute coronary syndrome by metabolic biomarkers and a diagnostic kit thereof.

BACKGROUND

Coronary artery disease (CAD), also named ischemic heart disease, involves the atherosclerosis of artery supplying heart muscle, which is caused by vascular stenosis or plaque rupture and occlusion accompanying myocardial ischemia, hypoxia or necrosis. The disease can lead to a series of serious cardiovascular problems such as angina and myocardial infarction. CAD remains one of the main killers to human health with high morbidity, high disability rate, high recurrence rate, high mortality, and multiple comorbidities and thus it has been one of the main diseases threatening human health.

Based on pathophysiologic mechanisms, CAD is currently divided into stable coronary artery disease (i.e., stable angina pectoris, SA) and acute coronary syndrome (ACS). ACS is further divided into unstable angina pectoris (UA) and acute myocardial infarction (AMI). The emergence and progression of CAD are as follows: normal coronary artery (NCA), coronary atherosclerosis (CA), SA, UA, and AMI.

Coronary artery atherosclerosis is the main cause and early stage of CAD. Coronary atherosclerosis is a common progressive arterial disease. The lesions are mainly involved in the medium sized muscular arteries with arterial intimal lipid deposition and proliferation of smooth muscle cells, which can lead to the formation of local plaque and make the arteries hard. When the plaque ruptures, thrombosis, embolism and hemorrhage happen and lead to partial or complete occlusion of the involved arteries. They are seen as the complications of atherosclerosis clinically. Early stage of coronary artery atherosclerosis may emerge before 10 years old while it takes 20 to 30 years to form artery stenosis. Because of non-obvious clinical symptoms of atherosclerosis in early stage, it is not easy to be noticed or regarded. Therefore, the early prevention and diagnosis of coronary artery atherosclerosis can effectively prevent the occurrence of CAD.

Coronary angiography can accurately determine the degree of stenosis of coronary artery and it is the "gold standard" for diagnosis of CAD (research on the differences in clinical diagnosis of coronary heart disease by using coronary angiography gold standards and conventional diagnosis techniques, Shu Rongwen, et. al., Journal of Navy Medicine, 2015, 4). Unfortunately, the invasive coronary angiography based on intervention surgery is costly and can simply determine the degree of stenosis of coronary artery. Moreover, Doctors need to refer to the patients' electrocardiogram, echocardiography, treadmill exercise test, CT and other test results to make the final diagnosis, which may cause erroneous diagnosis or missed diagnosis because of subjective judgment of doctors or patients' unclear statement. This affects the prognosis of the patients a lot. To reduce the threat to patients' life and improve their life quality a cheap, non-invasive and simple diagnostic method with high diagnostic accuracy is urgently needed.

Metabolomics, as an important part of system biology, focuses on endogenous metabolites in organism and their changes with internal and external factors. It can analyze body fluids quickly and non-invasively such as blood and urine, and obtain the metabolites that indicate the various biochemical reactions from the differences in metabolic profiles. The commonly used analytical techniques currently include nuclear magnetic resonance (NMR), mass spectrometry (LC-MS/GC-MS) and so on. Because of the simplicity in sample preparation, high sensitivity and wide linear range, LC-MS/GC-MS is becoming a more and more commonly used technology in metabolomics investigations. Plasma analysis is a common diagnostic method in clinical and is widely used because of its simplicity, low cost, and relatively non-invasiveness.

Up to now, no studies on plasma metabolomic profiling for characterizing different types of CAD were reported. Plasma metabolomic profiling of people with normal coronary artery and patients with coronary artery atherosclerosis and various types of CAD is of high meaning for clinical diagnosis of CAD and differentiation of the various types of CAD in early stage.

SUMMARY OF THE INVENTION

Firstly, the invention aims to afford a panel of metabolic biomarkers for differential diagnosis of stable angina pectoris and acute coronary syndrome. The metabolic biomarkers coexisting in plasma can be analyzed simultaneously. Secondly, the invention aims to afford a method for sensitive analysis of the metabolic biomarkers. Thirdly, the invention aims to afford a detection kit of the metabolic biomarkers for differential diagnosis of stable angina pectoris and acute coronary syndrome, making the diagnosis more convenient and standardized.

The above aims are accomplished by the following technical solutions.

A panel of metabolic biomarkers for differential diagnosis of stable angina pectoris and acute coronary syndrome comprises one or more of the metabolic biomarkers, including malic acid, taurine, arachidonic acid, citramalic acid, methionine, pentadecanoic acid.

As an optimized technology, the panel of metabolic biomarkers for differential diagnosis of stable angina pectoris and acute coronary syndrome comprises any two of the metabolic biomarkers.

As an optimized technology, the panel of metabolic biomarkers for differential diagnosis of stable angina pectoris and acute coronary syndrome comprises any three of the metabolic biomarkers.

As an optimized technology, the panel of metabolic biomarkers for differential diagnosis of stable angina pectoris and acute coronary syndrome comprises any four of the metabolic biomarkers.

As an optimized technology, the panel of metabolic biomarkers for differential diagnosis of stable angina pectoris and acute coronary syndrome comprises any five of the metabolic biomarkers.

As an optimized technology, the panel of metabolic biomarkers for differential diagnosis of stable angina pectoris and acute coronary syndrome comprises all of the six metabolic biomarkers.

As an optimized technology, all the metabolic biomarkers are defined as plasma metabolic biomarkers.

Methods for qualitative or quantitative analysis of the panel of metabolic biomarkers for differential diagnosis of stable angina pectoris and acute coronary syndrome comprise LC-MS and/or GC-MS. LC-MS and GC-MS show low detection limit and high sensitivity and thus can analyze metabolic biomarkers in biosamples sensitively.

A detection kit for differential diagnosis of stable angina pectoris and acute coronary syndrome comprises the reference standards of the panel of metabolic biomarkers. The reference standards are individually packaged or packaged together. The detection kit can promote the diagnostic standardization and thus improve the convenience and reproducibility of the diagnostic method.

As an optimized technology the kit comprises the solvents for dissolving the reference standards and/or for extraction and enrichment of the panel of metabolic biomarkers.

An implementation of the application discloses a method of differentiating stable angina pectoris from acute coronary syndrome, including: obtaining a blood plasma sample from a patient; measuring a relative concentration of at least one metabolic biomarker in the blood plasma sample, wherein the at least one metabolic biomarker is selected from the group consisting of malic acid, taurine, arachidonic acid, citramalic acid, methionine, and pentadecanoic acid; calculating a differentiating value according to the relative concentration of at least one metabolic biomarker; comparing the differentiating value with a predefined critical value, if the differentiating value is more than the predefined critical value, the patient has the acute coronary syndrome, otherwise, the patient has the stable angina pectoris.

An implementation of the application discloses a diagnostic kit for differentiating stable angina pectoris from acute coronary syndrome, including: a first container having a reference substance of 2-isopropyl malic acid, used for adding into a blood plasma sample to prepare into the blood plasma sample having an internal standard; a second container separate from the first container, the second container having at least one metabolic biomarker, wherein the at least one metabolic biomarker is selected from the group consisting of malic acid, taurine, arachidonic acid citramalic acid, methionine, and pentadecanoic acid, wherein the at least one metabolic biomarker is used for preparing a reference solution for UPLC-Q/TOF-MS analysis.

An implementation of the application discloses a method for differentiating SA patients from ACS patients, including: profiling plasma samples by UPLC-Q/TFQ-MS or GC-Q/MS, wherein an extraction solvent is selected based on a variable importance to projection value, wherein a higher variable importance to projection value indicates a better extraction solvent; using OPLS-DA to search for metabolites that contribute to the metabolic profiles of the SA patients and the ACS patients, having the variable importance to projection value higher than 1 and having p-value lower than 0.01; identifying structures of differential metabolites based on the molecular weights in HMDB and Metline databases; identifying ACS patients by detecting six differential metabolites having up-regulated and down-regulated trends, wherein the six differential metabolites are malic acid, taurine, arachidonic acid, citramalic acid, methionine, and pentadecanoic acid, wherein the malic acid and the citramalic acid are down-regulated by 0.7 to 0.8 times, and the taurine, the arachidonic acid, methionine, and pentadecanoic acid are up-regulated by 0.7 to 0.8 times.

The Advantages of this Invention

Firstly the metabolic biomarkers provided by the invention can accurately distinguish stable angina pectoris from acute coronary syndrome. According to the receiver operating characteristic (ROC) analysis, better prediction accuracy is obtained with AUC closer to 1.0 in the case of AUC higher than 0.5. AUC between 0.5~0.7 means lower diagnostic accuracy; AUC between 0.7~0.9 means certain diagnostic accuracy; AUC higher than 0.9 means high diagnostic accuracy. It is proved that single one of the metabolic biomarkers published by the invention offered AUC larger than 0.7 while combinations of the metabolic biomarkers offered AUC closer to 1 with better diagnostic accuracy. Combinations of all the six metabolic biomarkers offered AUC closest to 1 with the best diagnostic accuracy.

Secondly, the analytical method provided in the invention for the metabolic biomarkers is sensitive and accurate with robust reliability.

Thirdly, the detection kit is capable of differential diagnosis of SA and ACS and it can improve the diagnostic convenience and promote the diagnostic standardization.

DETAILED DESCRIPTION OF THE EMBODIMENTS

Figure 1:
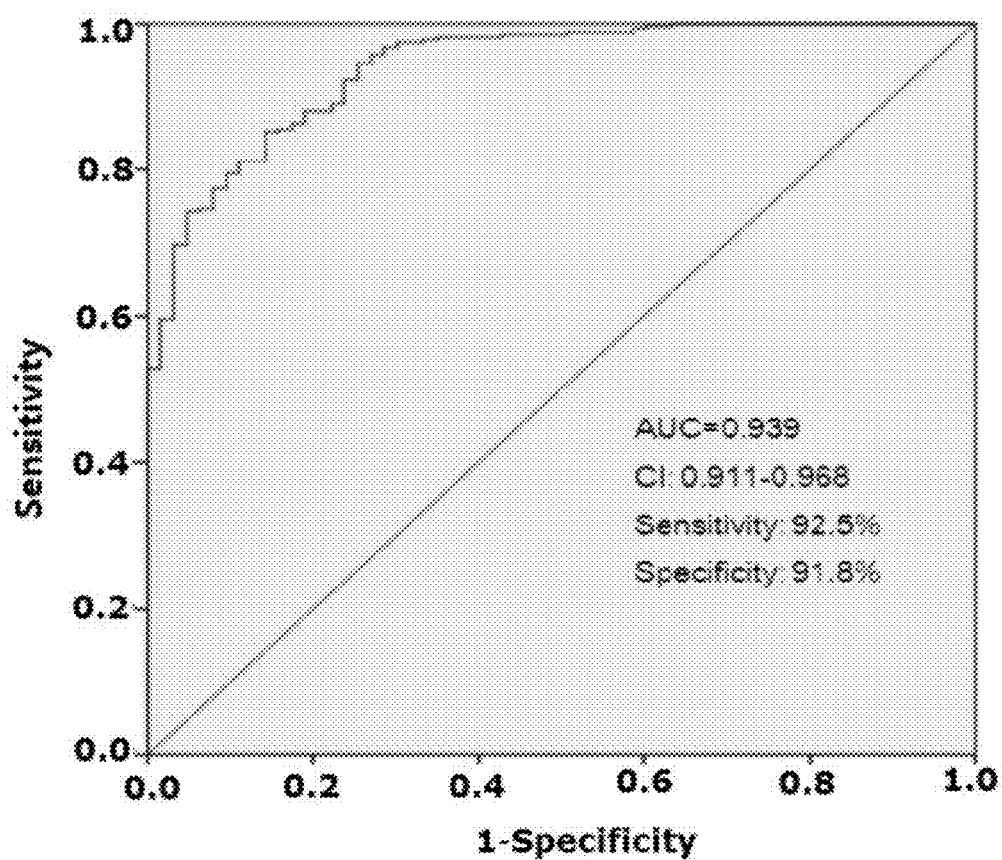
FIG. 1 shows a receiver operating curve for differentiating SA from ACS by taurine, arachidonic acid and methionine.

Several detailed cases for the applications of this invention are provided below. If not clarified, all the instruments and reagents are conventional, and all the operations used are public to a person skilled in the art.

Plasma Metabolomic Profiling of SA Patients and ACS Patients

Part One: Samples and Methods

1. Plasma Samples

Peripheral venous blood plasma of 280 SA patients, 320 ACS patients and 350 NCA enrolled from Jiangsu province hospital between September 2010 and June 2015 was collected. All the patients had signed the patient informed consent. All the SA patients, ACS patients and NCA were confirmed by coronary angiography. The ages and genders of NCA matched with those of SA and ACS patients. All the included patients had normal heart, lung, liver, kidney function and normal hematopoiesis.

Fasting blood was collected.

2. Reagents

Acetonitrile and formic acid (UPLC grade) were purchased from ROE company (USA). Methanol and chloroform (HPLC grade) were purchased from Jiangsu hanbon Science & Technology. Chlorinated methoxyamine and N-methyl-N-(trimethylsilyl)trifluoroacetamide (containing 1% trimethyl chlorosilane) were purchased from Sigma-Aldrich (USA). Deionized water was prepared by Milli-Q ultra pure water system (Millipore, USA). The reference standards of malic acid, taurine, arachidonic acid, citramalic acid, methionine and pentadecanoic acid were purchased from Sigma-Aldrich (USA).

3. Plasma Metabolomic Profiling 3.1. Profiling by UPLC-Q/TOF-MS 3.1.1. Sample Preparation Response surface method (RSM) was applied to optimize the extraction solvent. The extraction and enrichment efficiency of metabolites in plasma with acetonitrile, methanol, ethanol, chloroform and water was investigated to get more peak numbers and larger total peak area in both ESI+ and ESI− modes. Data were evaluated by multivariate analysis, and variable importance to projection (VIP value) in PLS model was applied to reflect the importance of variables to model response. The VIP values of acetonitrile, methanol, ethanol, chloroform, water were 1.503, 0.802, 0.651, 0.688, 0.987 respectively and acetonitrile got the best extraction efficiency. So acetonitrile was chosen as extraction solvent to extract plasma samples.

100 µL plasma was added to a 1.5 mL centrifuge tube, 400 µL acetonitrile was added, mixed 30 seconds by vortex, centrifugated for 10 minutes at 13,000 r/min at 4° C. Then, 200 µL supernatant was transferred to another 1.5 mL centrifuge tube, dried the liquid with nitrogen at room temperature and 300 µL 20% acetonitrile water solution was used to dissolve the residue.

3.1.2. Experimental Parameters

Parameters of UPLC-Q/TOF-MS

Liquid chromatographic separation for processed plasma was achieved on a 100×2.1 mm Waters BEH C18 column (particle size 1.7 µm) using a 1290 Infinity System (USA). Column temperature was 25° C. Temperature of injection chamber was room temperature. Injection volume was 2 µL. Mobile phase A was 0.1% formic acid-water solution (V/V) and mobile phase B was 0.1% formic acid-acetonitrile solution (V/V) in both ESI+ and ESI− modes. Linear gradient elution condition: 0~1 min, 0~30% mobile phase B; 1~3 min, 30~60% mobile phase B; 3~8 min, 60~90% mobile phase B; 8~9 min, 90~100% mobile phase B; 9~10 min, 100% mobile phase B. Flow rate was 0.3 mL/min. The eluent was totally directed to the mass spectrometry detector.

Mass spectrometry was performed on a 6530 Quadrupole-Time of Flight system (all devices from Agilent Technologies, USA). Detection mode. ESI+ and ESI−; flow rate of drying gas, 7 L/min; temperature of drying gas, 300° C.; ionization temperature, 100° C.; capillary voltage, 3000V in both ESI+ and ESI− modes; collision voltage, 100V. Dry gas and cone gas were high purity nitrogen gas. Data were acquired three times per second in full scan mode. Scan mass range was set between m/z 100-1000 Da.

3.2. Profiling by GC-Q/MS 3.2.1. Sample Preparation

200 µL plasma was added to a 1.5 mL centrifuge tube, 50 µL citramalic acid solution (1 mg/mL) was added as Internal standard, then 400 µL mixed solution of methanol, chloroform and water (2.5:1:1, V/V/V) was added, then shook 30 minutes at 1200 r/min incubated in constant temperature (70° C.) metal bath, centrifugated for 5 minutes at 16,000 g at 4° C. Then, 500 µL supernatant was transferred to another 1.5 mL centrifuge tube, added 500 µL distilled water, mixed by vortex, centrifugated for 5 minutes at 16,000 g at 4µ, 500 µL supernatant was transferred to another 1.5 mL centrifuge tube, dried the liquid with nitrogen at room temperature, 80 µL methoxamine pyridine solution was used to dissolve the residue and oximated 8 hours at 50° C. After that, added 60 µL N-methyl-N-(trimethylsilyl)trifluoroacetamide and reacted 2 hours at 70° C.

3.2.2 Experimental Parameters

Parameters of GC-Q/MS. GC-Q/MS was performed on Agilent 7890B-5977A gas chromatography/mass spectrometer (GC/MS, USA). Capillary column: HP-SMS (30.0 m×0.25 mm, thickness 0.25 µm). Carrier gas was high purity helium and its flow rate was 1.0 mL/min. Injection volume was 2 µL. By temperature programming, the initial oven temperature was 80° C., then increased to 300° C. at a rate of 5° C./min and held for 6 min. Splitless injection, the injector temperature, 300° C.; interface temperature, 300° C.; source temperature, 200° C.; electron energy, 50 eV; solvent delay, 3 min. The MS detector was performed in full-scan reaction monitoring mode and recorded across the range m/z 30-600 Da.

4. Data Processing and Analysis

The acquired MS data from * and GC-Q/MS were exported to SIMCA software (version 13.0.2, Umetrics). The OPLS-DA (orthogonal partial least squares-discriminant analysis) model was established to search for the metabolites that contributed a lot to the metabolic profiles between SA patients and ACS patients with VIP value higher than 1.0 and p value lower than 0.01.

The structures of the differential metabolites were preliminarily identified based on exact molecular weights in HMDB (http://www.hmdb.ca/) and Metline (http://metlin.scripps.edu/) databases and MS/MS spectra from mass spectroscopy. The structures were confirmed with the molecular weights, chromatographic retention times and multi stage MS spectra of the purchased reference standards.

Part Two: Results

Six differential metabolites were screen out including malic acid, taurine, arachidonic acid, citramalic acid, methionine, pentadecanoic acid.

Compared with SA Patients, the six differential metabolites with up-regulated or down-regulated trend were identified in the plasma of ACS Patients. It was proved that malic acid and citramalic acid down-regulated 0.7~0.8 times while taurine, arachidonic acid, methionine and pentadecanoic acid up-regulated 0.7~0.8 times in plasma of ACS patients compared with those of SA patients by quantitative analysis with reference standards. Thus it can be seen, the levels of the above six differential metabolites were significantly different between SA Patients and ACS Patients. The six differential metabolites can be used as metabolic biomarkers for differential diagnosis of SA and ACS.

Validation of the Diagnostic Ability by Using the Six Differential Metabolites to Distinguish SA from ACS by ROC Analysis Receiver operating curve (ROC) analysis was applied to validate the possibility of using the six differential metabolites to distinguish SA from ACS ACS. Single use of malic acid, taurine, arachidonic acid, citramalic acid, methionine, pentadecanoic acid provided clinically diagnostic value of SA vs. ACS with AUC>0.7. When combined, the more metabolites, the larger of AUC. The highest AUC of 0.987 was obtained when all of the six metabolites were combined to distinguish SA vs. ACS with sensitivity 96.8% and specificity 97.7% using optimal cut-off value. The AUC, sensitivity and specificity of ROC analysis with single metabolite or combination of any two to five metabolites were listed in table 1 to 3.

TABLE 1

Single use of the 6 differential metabolites to distinguish SA from ACS

| Single metabolite | AUC | Sensitivity | Specificity |
|---|---|---|---|
| Malic acid | 0.881 | 88.0% | 89.2% |
| Taurine | 0.868 | 84.7% | 85.9% |
| Arachidonic acid | 0.846 | 82.5% | 83.7% |
| Citramalic acid | 0.809 | 78.8% | 80.0% |
| Methionine | 0.793 | 77.2% | 78.4% |
| Pentadecanoic acid | 0.772 | 75.1% | 76.3% |

TABLE 2

Combination of any two of the 6 differential metabolites to distinguish SA from ACS

| Combined metabolites | | AUC | Sensitivity | Specificity |
|---|---|---|---|---|
| Malic acid | Taurine | 0.916 | 92.6% | 93.3% |
| | Arachidonic acid | 0.909 | 91.0% | 92.9% |
| | Citramalic acid | 0.905 | 90.3% | 91.1% |
| | Methionine | 0.899 | 89.8% | 90.6% |
| | Pentadecanoic acid | 0.896 | 89.3% | 89.9% |
| Taurine | Arachidonic acid | 0.892 | 88.8% | 89.4% |
| | Citramalic acid | 0.889 | 87.6% | 89.1% |
| | Methionine | 0.884 | 87.1% | 87.9% |
| | Pentadecanoic acid | 0.881 | 86.4% | 87.1% |
| Arachidonic acid | Citramalic acid | 0.879 | 86.7% | 86.5% |
| | Methionine | 0.869 | 85.5% | 86.3% |
| | Pentadecanoic acid | 0.865 | 84.8% | 86.0% |
| Citramalic acid | Methionine | 0.848 | 83.1% | 85.0% |
| | Pentadecanoic acid | 0.842 | 82.7% | 83.4% |
| Methionine | Pentadecanoic acid | 0.831 | 80.8% | 81.6% |

TABLE 3

Combination of any three to five of the 6 differential metabolites to distinguish SA from ACS

| Combined numbers | AUC | Sensitivity | Specificity |
|---|---|---|---|
| Three | ≥0.921 | ≥92.2% | ≥91.6% |
| Four | ≥0.933 | ≥92.7% | ≥93.3% |
| Five | ≥0.937 | ≥95.0% | ≥94.8% |

Table 1 shows that single use of the 6 differential metabolites provided clinically diagnostic value of SA vs. ACS with AUC>0.7. Table 2 shows that any two of the six differential metabolites provided high AUC with high sensitivity and specificity with potential clinically diagnostic value. Table 3 shows that any three to five metabolites of the six differential metabolites provided higher AUC than any two of the six differential metabolites with potential clinically diagnostic value.

Therefore, the six differential metabolites can be used as metabolic biomarkers for differential diagnosis of SA vs. ACS.

Preparation of Detection Kit

Detection kits were prepared on the basis of the metabolic biomarkers provided by the invention. The detection kit includes the following constituent.

Reference standards of the metabolic biomarkers are included. They are malic acid, taurine, arachidonic acid, citramalic acid, methionine and pentadecanoic acid. They are individually packaged.

Solvents to extract the metabolic biomarkers from plasma are included. They are pure acetonitrile and 20% acetonitrile water solution for sample preparation in UPLC-Q/TOF-MS analysis, mixed solution of methanol, chloroform, water (2.5:1:1, V/V/V), methoxamine pyridine solution and N-methyl-N-(trimethylsilyl)trifluoroacetamide for sample preparation in GC-Q/MS analysis. In UPLC-Q/TOF-MS analysis, 20% acetonitrile water solution can be used as the solvent to dissolve the reference standards. In GC-Q/MS analysis, the standard solutions are prepared as sample preparation.

Internal standard citramalic acid is included.

Of course, not all the six metabolic biomarkers are required. The detection kit may include some of them. The reference standards are individually packaged or packaged together.

The detection kit is designed based on the metabolic biomarkers published by the invention, so it can be applied to distinguish SA from ACS.

In summary, the invention effectively overcomes the disadvantages in the existing technology with high industrial potential.

Method of Differentiating SA from ACS

A first embodiment of method of differentiating SA from ACS is provided, and includes the following steps:

Step 1, Peripheral venous blood plasma of a patient is collected.

Step 2, An internal standard 2-isopropyl malic acid is added into the blood plasma to obtain the blood plasma having the internal standard at a concentration of 1 μg/ml. Specifically, the internal standard has a concentration of 1 μg/ml in the blood plasma.

Step 3, The blood plasma having the internal standard is prepared into a sample solution for UPLC-Q/TOF-MS analysis. The preparation method includes the following steps: 100 μL of plasma having the internal standard is put into a centrifuge tube of 1.5 mL, 400 μL of acetonitrile is then added into the centrifuge tube. The solution is mixed for 30 seconds by vortex, and then centrifugated for 10 minutes at 13,000 r/min at 4° C. 200 μL of the supernatant is transferred to another centrifuge tube of 1.5 mL, and dried with nitrogen at room temperature. The residues are dissolved by 300 μL of 20% acetonitrile aqueous solution.

Step 4, A certain amount of 2-isopropyl malic acid, taurine, arachidonic acid and methionine reference substances (the purities of these reference substances are no less than 98%) are dissolved by 20% acetonitrile aqueous solution (i.e., the same solvent for the sample solution) to prepare into a reference solution for UPLC-Q/TOF-MS analysis.

Step 5, The sample solution and the reference solution are analyzed by UPLC-Q/TOF-MS. The peak areas of the extracted ion chromatogram of taurine, arachidonic acid and methionine and the peak area of the extracted ion chromatogram of 2-isopropyl malic acid in the sample solution are measured, the ratios of the peak areas of the extracted ion chromatogram of taurine, arachidonic acid and methionine to the peak area of the extracted ion chromatogram of 2-isopropyl malic acid are used as relative concentrations of taurine, arachidonic acid and methionine.

Step 6, The relative concentrations of taurine, arachidonic acid and methionine are substituted in the binary logistic regression formula: $1/(1+\exp[(-6.487+24.535\times$ a relative concentration of taurine$+0.064\times$ a relative concentration of arachidonic acid$-3.119\times$ a relative concentration of methionine)]) to obtain the result of the formula, which is used for determining the disease category, for example, SA or ACS. The result of the formula is named as "differentiating value".

Step 7, If the differentiating value is smaller than a diagnostic threshold of 0.591, then this patient has SA. If the differentiating value is larger than 0.591 (i.e., the optimal cut-off value), then this patient has ACS.

A second embodiment of method of differentiating SA from ACS is provided, and includes the following steps:

Step 1, Peripheral venous blood plasma of a patient is collected.

Step 2, An internal standard 2-isopropyl malic acid is added into the blood plasma to obtain the blood plasma having the internal standard at a concentration of 1 μg/ml.

Step 3, The blood plasma having the internal standard is prepared into a sample solution for UPLC-QTOF-MS analysis. The preparation method includes the following steps: 100 μL of plasma having the internal standard is put into a centrifuge tube of 1.5 mL, 400 μL of acetonitrile is then added into the centrifuge tube. The solution is mixed for 30 seconds by vortex, and then centrifugated for 10 minutes at 13,000 r/min at 4° C. 200 μL of the supernatant is transferred to another centrifuge tube of 1.5 mL, and dried with nitrogen at room temperature. The residues are dissolved by 300 μL of 20% acetonitrile aqueous solution.

Step 4, A certain amount of 2-isopropyl malic acid, taurine, arachidonic acid and methionine reference substances are dissolved by 20% acetonitrile aqueous solution (i.e., the same solvent for the sample solution) to prepare into a reference solution for UPLC-Q/TOF-MS analysis.

Step 5, The sample solution and the reference solution are analyzed by UPLC-Q/TOF-MS. The peak areas of the extracted ion chromatogram of malic acid, taurine, arachidonic acid, citramalic acid, methionine and pentadecanoic acid and the peak area of the extracted ion chromatogram of 2-isopropyl malic acid in the sample solution are measured, the ratios of the peak areas of the extracted ion chromatogram of malic acid, taurine, arachidonic acid, citramalic acid, methionine and pentadecanoic acid to the peak area of the extracted ion chromatogram of 2-isopropyl malic acid are used as relative concentrations of malic acid, taurine, arachidonic acid, citramalic acid, methionine and pentadecanoic acid.

Step 6, The relative concentrations of malic acid, taurine, arachidonic acid, citramalic acid, methionine and pentadecanoic acid are substituted in the binary logistic regression formula: 1/1+exp[(−3.893+32.540× a relative concentration of malic acid+0.046× a relative concentration of taurine−3.926× a relative concentration of arachidonic acid+0.045× a relative concentration of citramalic acid+0.028× a relative concentration of methionine−0.022× a relative concentration of pentadecanoic acid)] to obtain the result of the formula (i.e., differentiating value).

Step 7, If the differentiating value of the formula is smaller than a diagnostic threshold of 0.572, then this patient has SA. If the differentiating value is larger than 0.572, then this patient has ACS.

Method of Validating the Diagnostic Effects

A first embodiment of method of validating the diagnostic effects of a combination of taurine, arachidonic acid and methionine for differentiating SA from ACS is provided, and includes the following steps:

Step 1, The relative concentrations of taurine, arachidonic acid and methionine of the samples in a training group are respectively measured.

The step 1 further includes the steps as below:

Step 1.1, Peripheral venous blood plasma of 280 SA patients and 320 ACS patients from Jiangsu province hospital was collected as training group samples during the period from September 2010 to June 2015.

Step 1.2, An internal standard 2-isopropyl malic acid is added into the blood plasma to obtain the blood plasma having the internal standard at a concentration of 1 μg/ml.

Step 1.3, The blood plasma having the internal standard is prepared into a sample solution for UPLC-Q/TOF-MS analysis. The preparation method includes the following steps: 100 μL of plasma having the internal standard is put into a centrifuge tube of 1.5 mL, 400 μL of acetonitrile is then added into the centrifuge tube. The solution is mixed for 30 seconds by vortex, and then centrifugated for 10 minutes at 13,000 r/min at 4° C. 200 μL of the supernatant is transferred to another centrifuge tube of 1.5 mL, and dried with nitrogen at room temperature. The residues are dissolved by 300 μL of 20% acetonitrile aqueous solution.

Step 1.4, A certain amount of 2-isopropyl malic acid, taurine, arachidonic acid and methionine reference substances are dissolved by 20% acetonitrile aqueous solution to prepare into a reference solution for UPLC-Q/TOF-MS analysis.

Step 1.5, The sample solution and the reference solution are analyzed by UPLC-Q/TOF-MS. The peak areas of the extracted ion chromatogram of taurine, arachidonic acid and methionine and the peak area of the extracted ion chromatogram of 2-isopropyl malic acid in the sample solution are measured, the ratios of the peak areas of the extracted ion chromatogram of taurine, arachidonic acid and methionine to the peak area of the extracted ion chromatogram of 2-isopropyl malic acid are used as relative concentrations of taurine, arachidonic acid and methionine.

To perform the step 1.5, a liquid chromatographic separation for processing the plasma is made on a 100 mm×2.1 mm Waters BEH C18 column (particle size 1.7 μm) using a highly efficient liquid chromatography system (UPLC, Agilent 1290, USA). Column temperature is 25° C. The temperature of an injection chamber is room temperature. An injection volume is 2 μL. Mobile phases are composed of a mobile phase A and a mobile phase B. The mobile phase A is 0.1% formic acid aqueous solution (V/V) and the mobile phase B is 0.1% formic acid-acetonitrile solution. Linear gradient elution conditions are provided: the mobile phase B is 0~30% within 0~1 min; the mobile phase B are linearly increased to 60% within 2 min, the mobile phase B changes to 90% within 3~8 min; the mobile phase B are linearly increased to 100% within 8~9 min and kept for 1 min. The flow rate is 0.3 mL/min. All the eluent is directly output to the mass spectrometry detector.

The mass spectrometry is performed on Agilent 6530 Q/TOF-MS system, working in a ESI negative ion mode. The flow rate of drying gas is 7 L/min at a temperature of 300° C. The drying gas and cone gas are both highly pure nitrogen. The ionization temperature is 100° C. The capillary voltage is 3000V. The collision voltage is 100V. The data are acquired three times per second in a full scan mode. The scan mass range is set within m/z 100-1000 Da.

Step 1.6, The relative concentrations of taurine, arachidonic acid and methionine in the sample solution are used as relative concentrations of taurine, arachidonic acid and methionine of the samples in the training group.

Step 2, A binary logistic regression formula is built.

The step 2 includes the following steps: The blood plasma of SA patient samples in the training group is included in Group 1, while the blood plasma of ACS patient samples in the training group is included in Group 2. The relative concentrations of taurine, arachidonic acid and methionine in the two groups are analyzed with binary logistic regression to obtain the binary logistic regression formula, which is 1/(1+exp[(Constant+coefficient 1× the relative concentration of taurine+coefficient 2× the relative concentration of arachidonic acid+coefficient 3× the relative concentration of methionine)]).

Constant and coefficient values are provided in the following table:

|  | Coefficient | Standard Error | p value |
| --- | --- | --- | --- |
| Taurine | 24.535 | 3.561 | <0.001 |
| Arachidonic acid | 0.064 | 0.011 | <0.001 |
| Methionine | −3.119 | 1.188 | 0.009 |
| Constant | −6.487 | 1.292 | <0.001 |

Step 3, ROC (Receiver operating curve) is made and the optimal cut-off value is determined.

The step 3 includes the following steps:

Step 3.1, The relative concentrations of taurine, arachidonic acid and methionine of each sample in the training group are substituted in the binary logistic regression formula to obtain the result of the formula (i.e., differentiating value) of each sample.

Step 3.2, The differentiating value of each sample in the training group is used as an inspection variable, and the group category (Group 1 or Group 2) is used as a state variable to draw a ROC. The area under the curve (AUC) is 0.939.

Step 3.3, The Youden index of each point on the curve is calculated according to horizontal and vertical coordinates of ROC. Youden index=Specificity+Sensitivity−1. The point with the value of 0.591 corresponding to the maximum Youden index is determined as the critical value (the optimal cut-off value) for differentiating SA from ACS. The sensitivity corresponding to the optimal cut-off value is 92.5%, and the specificity corresponding to the optimal cut-off value is 91.8%. ROC is shown in FIG. 1.

Step 4, The relative concentrations of taurine, arachidonic acid and methionine of the samples in a validation group are respectively measured.

The step 4 includes the following steps:

Peripheral venous blood plasma of 70 SA patients and 270 ACS patients from Subei people's hospital was collected as validation group samples during the period from September 2010 to June 2015. The step of measuring relative concentrations of taurine, arachidonic acid and methionine of the samples in the validation group are the same as the step 1.

Step 5, The accuracy rate of differentiating SA from ACS by the optimal cut-off value as the critical value is calculated.

The step 5 includes the following steps:

The relative concentrations of taurine, arachidonic acid and methionine of each sample in the validation group are substituted in the binary logistic regression formula to obtain the result of the formula (i.e., differentiating value) of each sample. If the differentiating value of a sample in the validation group is smaller than 0.591, then this sample has SA. By contrast, if the differentiating value of a sample in the validation group is larger than 0.591, then this sample has ACS.

Next, the accuracy rate of differentiating SA from ACS by the relative concentrations of taurine, arachidonic acid and methionine is calculated.

Accuracy rate (%)=Sample number of correct prediction/Total sample number in the validation group×100%

It is proved that the accuracy rate of differentiating SA from ACS by the relative concentrations of taurine, arachidonic acid and methionine is up to 91.8%.

A second embodiment of method of validating the diagnostic effects of a combination of malic acid, taurine, arachidonic acid, citramalic acid, methionine and pentadecanoic acid for differentiating SA from ACS is provided, and includes the following steps:

Step 1, The relative concentrations of malic acid, taurine, arachidonic acid, citramalic acid, methionine and pentadecanoic acid of the samples in a training group are respectively measured.

The step 1 further includes the steps as below:

Step 1.1, Peripheral venous blood plasma of 280 SA patients and 320 ACS patients from Jiangsu province hospital was collected as training group samples during the period from September 2010 to June 2015.

Step 1.2, An internal standard 2-isopropyl malic acid is added into the blood plasma to obtain plasma having the internal standard at a concentration of 1 µg/ml.

Step 1.3, The blood plasma having the internal standard is prepared into a sample solution for UPLC-Q/TOF-MS analysis. The preparation method includes the following steps: 100 µL of plasma having the internal standard is put into a centrifuge tube of 1.5 mL, 400 µL of acetonitrile is then added into the centrifuge tube. The solution is mixed for 30 seconds by vortex, and then centrifugated for 10 minutes at 13,000 r/min at 4° C. 200 µL of the supernatant is transferred to another centrifuge tube of 1.5 mL, and dried with nitrogen at room temperature. The residues are dissolved by 300 µL of 20% acetonitrile aqueous solution.

Step 1.4, A certain amount of malic acid, taurine, arachidonic acid, citramalic acid, methionine and pentadecanoic acid as reference substances are dissolved by 20% acetonitrile aqueous solution to prepare into a reference solution for UPLC-Q/TOF-MS analysis.

Step 1.5, The sample solution and the reference solution are analyzed by UPLC-Q/TOF-MS. The peak areas of the extracted ion chromatogram of malic acid, taurine, arachidonic acid, citramalic acid, methionine and pentadecanoic acid and the peak area of the extracted ion chromatogram of 2-isopropyl malic acid in the sample solution are measured, the ratios of the peak areas of the extracted ion chromatogram of malic acid, taurine, arachidonic acid, citramalic acid, methionine and pentadecanoic acid to the peak area of the extracted ion chromatogram of 2-isopropyl malic acid are used as relative concentrations of malic acid, taurine, arachidonic acid, citramalic acid, methionine and pentadecanoic acid.

To perform the step 1.5, a liquid chromatographic separation for processing the plasma is made on a 100 mm×2.1 mm Waters BEH C18 column (particle size 1.7 µm) using a highly efficient liquid chromatography system (UPLC, Agilent 1290, USA). Column temperature is 25° C. The temperature of an injection chamber is room temperature. An injection volume is 2 µL. Mobile phases are composed of a mobile phase A and a mobile phase B. The mobile phase A is 0.1% formic acid aqueous solution (V/V) and the mobile phase B is 0.1% formic acid-acetonitrile solution. Linear gradient elution conditions are provided: the mobile phase B is 0~30% within 0~1 min; the mobile phase B are linearly increased to 60% within 2 min, the mobile phase B changes to 90% within 3~8 min: the mobile phase B are linearly increased to 100% within 8~9 min and kept for 1 min. The flow rate is 0.3 mL/min. All the eluent is directly output to the mass spectrometry detector.

The mass spectrometry is performed on Agilent 6530 Q/TOF-MS system, working in a ESI negative ion mode. The flow rate of drying gas is 7 L/min at a temperature of 300° C. The drying gas and cone gas are both highly pure nitrogen. The ionization temperature is 100° C. The capillary voltage is 3000V. The collision voltage is 100V.

The data are acquired three times per second in a full scan mode. The scan mass range is set within m/z 100-1000 Da.

Step 1.6, The relative concentrations of malic acid, taurine, arachidonic acid, citramalic acid, methionine and pentadecanoic acid in the sample solution are used as relative concentrations of malic acid, taurine, arachidonic acid, citramalic acid, methionine and pentadecanoic acid of the samples in the training group.

Step 2, A binary logistic regression formula is built.

The step 2 includes the following steps: The blood plasma of SA patient samples in the training group is included in Group 1, while the blood plasma of ACS patient samples in the training group is included in Group 2. The relative concentrations of malic acid, taurine, arachidonic acid, citramalic acid, methionine and pentadecanoic acid in the two groups are analyzed with binary logistic regression to obtain the binary logistic regression formula, which is 1/(1+exp [(Constant+coefficient 1× the relative concentration of malic acid+coefficient 2× the relative concentration of taurine+ coefficient 3× the relative concentration of arachidonic acid+ coefficient 4× the relative concentration of citramalic acid+ coefficient 5× the relative concentration of methionine+ coefficient 6× the relative concentration of pentadecanoic acid)]).

Constant and coefficient values are provided in the following table:

|  | Coefficient | Standard Error | p value |
| --- | --- | --- | --- |
| malic acid | 32.540 | 8.150 | <0.001 |
| taurine | 0.046 | 0.017 | 0.009 |
| arachidonic acid | −3.926 | 2.498 | 0.001 |
| citramalic acid | 0.045 | 0.014 | 0.001 |
| methionine | 0.028 | 0.063 | 0.007 |
| pentadecanoic acid | −0.022 | 0.007 | 0.001 |
| Constant | −3.893 | 3.957 | 0.003 |

Step 3, ROC (Receiver operating curve) is made and the optimal cut-off value is determined.

The step 3 includes the following steps:

Step 3.1, The relative concentrations of malic acid, taurine, arachidonic acid, citramalic acid, methionine and pentadecanoic acid of each sample in the training group are substituted in the binary logistic regression formula to obtain the result of the formula (i.e., differentiating value) for each sample.

Step 3.2, The differentiating value of each sample in the training group is used as an inspection variable, and the group category (Group 1 or Group 2) is used as a state variable to draw a ROC. The area under the curve (AUC) is 0.987.

Figure 2:
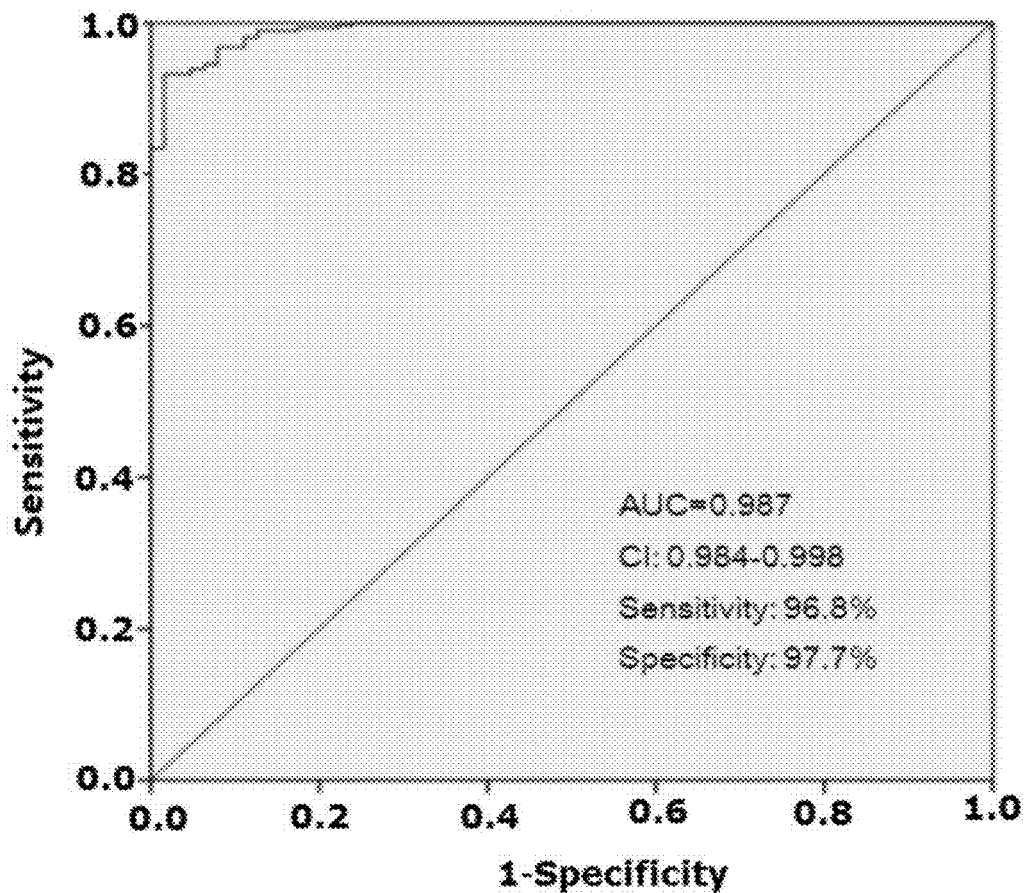
FIG. 2 shows another receiver operating curve for differentiating SA from ACS by malic acid, taurine, arachidonic acid, citramalic acid, methionine and pentadecanoic acid.

Step 3.3, The Youden index of each point on the curve is calculated according to horizontal and vertical coordinates of ROC. Youden index=Specificity+Sensitivity−1. The point with the value of 0.572 corresponding to the maximum Youden index is determined as the critical value (the optimal cut-off value) for differentiating SA from ACS. The sensitivity corresponding to the optimal cut-off value is 96.8%, and the specificity corresponding to the optimal cut-off value is 97.7%. ROC is shown in FIG. 2.

Step 4, The relative concentrations of malic acid, taurine, arachidonic acid, citramalic acid, methionine and pentadecanoic acid of samples in a validation group are respectively measured.

The step 4 includes the following steps:

Peripheral venous blood plasma of 70 SA patients and 270 ACS patients from Subei people's hospital was collected as validation group samples during the period from September 2010 to June 2015. The step of measuring relative concentrations of malic acid, taurine, arachidonic acid, citramalic acid, methionine and pentadecanoic acid of the samples in the validation group are the same as the step 1.

Step 5, The accuracy rate of differentiating SA from ACS by the optimal cut-off value as the critical value is calculated.

The step 5 includes the following steps:

The relative concentrations of malic acid, taurine, arachidonic acid, citramalic acid, methionine and pentadecanoic acid of each sample in the validation group are substituted in the binary logistic regression formula to obtain the result of the formula (i.e., differentiating value) of each sample. If the differentiating value of a sample in the validation group is smaller than 0.572, then this sample has SA. By contrast, if the differentiating value of a sample in the validation group is larger than 0.572, then this sample has ACS.

Next, the accuracy rate of differentiating SA from ACS by the relative concentrations of malic acid, taurine, arachidonic acid, citramalic acid, methionine and pentadecanoic acid is calculated.

Accuracy rate (%)=Sample number of correct prediction/Total sample number in the validation group×100%

It is proved that the accuracy rate of differentiating SA from ACS by the relative concentrations of malic acid, taurine, arachidonic acid, citramalic acid, methionine and pentadecanoic acid is up to 92.4%.

Diagnostic Kit

A first embodiment of a diagnostic kit is provided. The diagnostic kit is used for differentiating SA from ACS by taurine, arachidonic acid, and methionine.

The diagnostic kit includes two separate containers A and B. The container A only has a reference substance of 2-isopropyl malic acid (the purity of 2-isopropyl malic acid is no less than 98%), while the container B includes a reference mixture of 2-isopropyl malic acid, taurine, arachidonic acid, and methionine (the purities of 2-isopropyl malic acid, taurine, arachidonic acid, and methionine are respectively no less than 98%). The 2-isopropyl malic acid of the container A is used for adding into the blood plasma to prepare into the blood plasma having the internal standard. The reference mixture of the container B is used for preparing the reference solution. The reference solution is used for discerning the chromatogram peaks of 2-isopropyl malic acid, taurine, arachidonic acid, and methionine in the sample solution, which is prepared by the blood plasma having the internal standard. The proportion of each substance in the reference mixture is not strictly defined and the diagnostic kit is used for qualitative analysis.

A second embodiment of a diagnostic kit is provided. The diagnostic kit is used for differentiating SA from ACS by malic acid, taurine, arachidonic acid, citramalic acid, methionine and pentadecanoic acid.

The diagnostic kit includes two separate containers A and B. The container A only has a reference substance of 2-isopropyl malic acid (the purity of 2-isopropyl malic acid is no less than 98%), while the container B includes a reference mixture of 2-isopropyl malic acid, malic acid, taurine, arachidonic acid, citramalic acid, methionine and pentadecanoic acid (the purities of 2-isopropyl malic acid, malic acid, taurine, arachidonic acid, citramalic acid, methionine and pentadecanoic acid are respectively no less than 98%). The 2-isopropyl malic acid of the container A is used for adding into the blood plasma to prepare into the blood plasma having the internal standard. The reference mixture of the container B is used for preparing the reference solution. The reference solution is used for discerning the chromatogram peaks of 2-isopropyl malic acid, malic acid, taurine, arachidonic acid, citramalic acid, methionine and pentadecanoic acid in the sample solution, which is prepared by the blood plasma having the internal standard. The proportion of each substance in the reference mixture is not strictly defined and the diagnostic kit is used for qualitative analysis.

Both the container A and the container B are sealed. In particular, the container B is filled with a mixture of nitrogen and argon at a volume ratio of 1:1~3:1 before it is sealed. The mixture of nitrogen and argon can effectively enhance the thermal stability and the light stability of the reference mixture in the container B.

In one implementation, the reference mixture of 2-isopropyl malic acid, malic acid, taurine, arachidonic acid, citramalic acid, methionine and pentadecanoic acid is sealed in a common transparent glass bottle and protected by a mixture of nitrogen and argon at a volume ratio of 1:1~3:1. If the glass bottle is put in an oven at 60±5° C. for 15 days, the total degradation rate (calculated with the formula as below) is lower than 0.5%. If the glass bottle is placed in a lighting incubator with a luminous intensity of 4500+500 Lx for 15 days, the total degradation rate is also lower than 0.5%. By contrast, in case that the glass bottle is filled with air instead of the mixture of nitrogen and argon, if the glass bottle is put in an oven at 60±5° C. for 15 days, the total degradation rate is over 55%. If the glass bottle is placed in a lighting incubator with a luminous intensity of 4500±500 Lx for 15 days, the total degradation rate is over 35%.

The total degradation rate formula is: Total degradation rate (%)=(1−sum of remaining content of each substance in the reference mixture/sum of initial content of each substance in the reference mixture)×100%.

If the reference mixture in the glass bottle is protected by a mixture of nitrogen and argon at a volume ratio of 1:1~3:1, then a common transparent container can be used as the container B. Besides, it is unnecessary for the container B to be kept away from the light or to be refrigerated. The reference mixture has a high stability, a long service life, and low package and storage costs.

It should be understood that the embodiments described above are only used to explain the present invention, but not to limit the present invention. The obvious modifications and variations derived from the spirit of the present invention also fall into the protection scope of the present invention.

What is claimed is:

1. A method of differentiating stable angina pectoris from acute coronary syndrome, comprising:
    obtaining a blood plasma sample from a patient;
    measuring a relative concentration of at least one metabolic biomarker in the blood plasma sample, wherein the at least one metabolic biomarker is selected from the group consisting of malic acid, taurine, arachidonic acid, citramalic acid, methionine, and pentadecanoic acid; wherein, the step of measuring a relative concentration of at least one metabolic biomarker in the blood plasma sample further comprises the following steps:
    a), adding an internal standard of 2-isopropyl malic acid into the blood plasma to obtain the blood plasma having the internal standard at a concentration of 1 µg/ml; b), preparing the blood plasma having the internal standard into a sample solution, using a solvent; c), dissolving a reference mixture using the solvent to prepare a reference solution, wherein the reference mixture includes 2-isopropyl malic acid and the at least one metabolic biomarker, and the purities of the 2-isopropyl malic acid and the at least one metabolic biomarker are no less than 98%; and d), analyzing the sample solution and the reference solution by UPLC-Q/TOF-MS, measuring a peak area of extracted ion chromatogram of the at least one metabolic biomarker and a peak area of extracted ion chromatogram of the 2-isopropyl malic acid in the sample solution, and using a ratio of the peak area of the extracted ion chromatogram of the at least one metabolic biomarker to the peak area of the extracted ion chromatogram of the 2-isopropyl malic acid as a relative concentration of the at least one metabolic biomarker;
    obtaining a differentiating value according to the relative concentration of at least one metabolic biomarker; wherein the differentiating value is a value calculated by a formula; and
    comparing the differentiating value with a predefined critical value, if the differentiating value is more than the predefined critical value, the patient has the acute coronary syndrome, otherwise, the patient has the stable angina pectoris, wherein the predefined critical value is determined according to the at least one metabolic biomarker.

2. The method of claim 1, wherein the at least one metabolic biomarker includes three metabolic biomarkers taurine, arachidonic acid and methionine, wherein the predefined critical value is 0.591.

3. The method of claim 2, wherein the differentiating value is calculated by the formula of $1/(1+\exp[(-6.487+24.535\times \text{a relative concentration of taurine}+0.064\times \text{a relative concentration of arachidonic acid} -3.119\times \text{a relative concentration of methionine})])$.

4. The method of claim 1, wherein the at least one metabolic biomarker includes six metabolic biomarkers malic acid, taurine, arachidonic acid, citramalic acid, methionine, and pentadecanoic acid, wherein the predefined critical value is 0.572.

5. The method of claim 4, wherein the differentiating value is calculated by the formula of $1/(1+\exp[(-3.893+32.540\times \text{a relative concentration of malic acid}+0.046\times \text{a relative concentration of taurine} -3.926\times \text{a relative concentration of arachidonic acid}+0.045\times \text{a relative concentration of citramalic acid}+0.028\times \text{a relative concentration of methionine} -0.022\times \text{a relative concentration of pentadecanoic acid})])$.

6. The method of claim 1, wherein the solvent is 20% acetonitrile aqueous solution.

* * * * *